(12) United States Patent
Muhle et al.

(10) Patent No.: US 7,226,789 B2
(45) Date of Patent: Jun. 5, 2007

(54) METHOD OF APPLYING NON-LINEAR DYNAMICS TO CONTROL A GAS-PHASE POLYETHYLENE REACTOR OPERABILITY

(75) Inventors: Michael E. Muhle, Kingwood, TX (US); Ke Nguyen, Knoxville, TN (US); Charles E.A. Finney, Knoxville, TN (US); Stuart C. Daw, Knoxville, TN (US)

(73) Assignee: Unication Technolofies, LLC, Houston, TX (US)

( * ) Notice: Subject to any disclaimer, the term of this patent is extended or adjusted under 35 U.S.C. 154(b) by 471 days.

(21) Appl. No.: 10/298,311

(22) Filed: Nov. 18, 2002

(65) Prior Publication Data
US 2003/0121330 A1   Jul. 3, 2003

(51) Int. Cl.
*G01N 31/10* (2006.01)
(52) U.S. Cl. .............................. 436/55; 436/37; 436/50
(58) Field of Classification Search .................. 422/62, 422/105, 108–112; 436/37, 50, 55
See application file for complete search history.

(56) References Cited

U.S. PATENT DOCUMENTS

| | | | |
|---|---|---|---|
| 4,336,227 A | 6/1982 | Koyama et al. | 422/111 |
| 4,803,251 A | 2/1989 | Goode et al. | 526/59 |
| 4,858,144 A * | 8/1989 | Marsaly et al. | 700/266 |
| 4,993,264 A * | 2/1991 | Cody et al. | 73/579 |
| 5,022,268 A * | 6/1991 | Wolf et al. | 73/602 |
| 5,435,972 A * | 7/1995 | Daw et al. | 422/108 |
| 5,436,304 A | 7/1995 | Griffin et al. | 526/68 |
| 5,648,581 A * | 7/1997 | Kubo et al. | 585/501 |
| 5,740,291 A * | 4/1998 | De Lasa et al. | 385/31 |
| 6,008,662 A * | 12/1999 | Newton et al. | 324/724 |
| 6,111,034 A * | 8/2000 | Goode et al. | 526/59 |
| 6,122,557 A | 9/2000 | Harrell et al. | 700/45 |
| 6,144,897 A | 11/2000 | Selliers | 700/269 |
| 6,384,157 B1 * | 5/2002 | Cai et al. | 526/88 |
| 6,548,610 B2 * | 4/2003 | Bartilucci et al. | 526/74 |
| 6,831,140 B2 * | 12/2004 | Muhle et al. | 526/74 |

FOREIGN PATENT DOCUMENTS

| | | |
|---|---|---|
| EP | 0 233 787 A1 | 8/1987 |
| EP | 0 385 788 A2 | 9/1990 |
| EP | 0 399 796 A2 | 11/1990 |
| EP | 882499 | 12/1998 |
| WO | WO 01/09196 A1 | 2/2001 |

OTHER PUBLICATIONS

Gyure, D. C. et al, Industrial & Engineering Chemistry Research 1987, 26, 938-944.*

(Continued)

*Primary Examiner*—Arlen Soderquist
(74) *Attorney, Agent, or Firm*—Osborne McKinney; Kevin M. Faulkner; Leandro Arechederra

(57) ABSTRACT

The present invention describes a method for determining reactor continuity of a polymerization reactor by non-linear dynamics. Specifically, the invention relates to a method of analyzing system variables to indicate gas phase reactor continuity in real-time and controlling the reactor continuity to maintain operability.

27 Claims, 14 Drawing Sheets

OTHER PUBLICATIONS

Blasetti, A. et al, Industrial & Engineering Chemistry Research 2001, 40, 4623-4632.*
Lau, I. T. et al, Fuel Processing Technology 1981, 4, 101-115.*
Jang, S.-S. et al, AIChE Journal 1987, 33, 26-35.*
Kage, H. et al, AIChE Symposium Series 1993, 296, 184-190.*
Schouten, J. C. et al, AIChE Journal 1998, 44, 48-60.*
Christofides, P. D., Industrial & Engineering Chemistry Research 1998, 37, 1893-1909.
Ali, E. M. et al, Industrial & Engineering Chemistry Research 1998, 37, 3414-3423.
Briens, C. L. et al, Powder Technology 1999, 102, 95-103.
Grace, J. R. et al, Canadian Journal of Chemical Engineering 1999, 77, 305-311.
Bai, D. et al, Industrial & Engineering Chemistry Research 1999, 38, 803-811.
Kaart, S. et al, Catalysis Today 1999, 48, 185-194.
Tsujimoto, H. et al, Powder Technology 2000, 113, 88-96.
Ghasem, N. M., Chemical Engineering & Technology 2000, 23, 133-140.
Ghasem, N. M., Chemical Engineering & Technology 2001, 24, 297-303.
Woo, K. J. et al, Chemical Engineering & Technology 2001, 24, 829-834.
van den Bleek, C. M. et al, Chemical Engineering Journal 1993, 53, 75-87.*
Hyanek, I. et al, Industrial & Engineering Chemistry Research 1995, 34, 3872-3877.*
Schouten, J. C. et al, Chemical Engineering Science 1996, 51, 1991-2000.*
Christofides, P. D. et al, Journal of Process Control 1997, 7, 313-328.*
Bakker, R. et al, Fractals 1997, 5, 523-530.
Kurtz, M. J. et al, Computers & Chemical Engineering 1998, 22, 1441-1459.
Van de Velde, E. F. et al, Proceedings of the Royal Society of London, Series A: Mathematical, Physical and Engineering Sciences 1991, 434, 341-367.
Elnashaie, S. S. E. H. et al, Chaos, Solitons & Fractals 1995, 5, 797-831.
Cassanello, M. et al, Industrial & Engineering Chemistry Research 1995, 34, 2971-2980.
Elnashaie, S. S. E. H. et al, Chaos, Solitons & Fractals 1996, 7, 1317-1331.
Elnashaie, S. S. E. H. et al, Chaos, Solitons & Fractals 1996, 7, 1955-1967.
Ohman, M. et al, Energy & Fuels 1998, 12, 90-94.
Strozzi, F. et al, AIChE Journal 1999, 45, 2429-2443.
Cody, G. D. et al, Powder Technology 2000, 110, 128-142.

* cited by examiner

METHOD OF APPLYING NON-LINEAR DYNAMICS TO CONTROL A GAS-PHASE POLYETHYLENE REACTOR OPERABILITY

BACKGROUND OF THE INVENTION

1. Field of the Invention

The invention relates to a method of controlling the continuity of a fluidized bed gas phase reactor by examining signal complexity. Specifically, the invention relates to a method of detecting sheeting in the reactor by employing non-linear dynamics to evaluate signal complexity and determine reactor continuity. The invention also relates to controlling the reactor continuity by determining a sheeting precursor state and allowing a counter measure to be applied to prevent sheeting occurrences.

2. Related Art

Recirculating fluid-bed reactors are particularly advantageous due to their uniform composition and temperature, ease of sampling and intensive mixing. Ideal reactor continuity requires stable and high production rates, an absence of sheeting occurrences (see U.S. Pat. Nos. 5,436,304 and 5,405,922, which are incorporated herein by reference), and consequently constant production rate. In a sheeting event, maintenance of fluid-bed reactors involves a complete shutdown that translates directly into lost production time. Unfortunately, methods are not known to prevent such catastrophic events.

Reactor operability results from a triad of intercalated parts: catalyst and process chemistry, surface and physical chemistry, and reaction engineering. The latter comprises catalyst delivery systems, particle growth, heat generation and removal, particle morphology, fluidization behavior, condensing mode effects, and process control. Of these factors, efficient removal of heat generated during reactor operation that exceeds rates of heat generation is the crux of understanding and maintaining reactor continuity.

Heat transfer is efficient provided the reaction environment is tailored to provide an acceptably wide thermal stability window at macroscale (whole system), microscale (intra-particle) and mesoscale (inter-particle) levels of operation. To completely control heat transfer, basic principles must be understood. It is widely known that heat transfer results from either conductive or convective mechanisms. This is described in terms of thermal conductivity and convective heat transfer coefficients. These variables are used to derive a Nusselt number (Nu), which has been correlated to single drops of evaporating liquids. It has generally been assumed that the same correlation applies to multi-phase gas-solid flow, however, the role of particle-particle interactions is neglected (mesoscale level). Ignoring the contribution suggests that the correlation is only valid for highly dilute systems. Recently, several reports on the multi-phase heat transfer process based on experimental and theoretical principles have emerged.

Despite the growing interest in the Nusselt number, recent computational fluid dynamics (CFD) studies point to the importance of particle-particle interactions in gas-phase polyethylene polymerization. Results of these studies indicate that a large temperature differential exists between small and larger particles and that inter-particle effects are more influential than an intra-particle gradient. This means that if two particles of approximately the same size make physical contact, a hot spot forms between them. Additionally, if small, highly active particles are shielded from the gas flow without any contact, rapid overheating of the particles occurs. Isolated particles are predicted to be thermally stable provided the reaction is at a constant polymerization rate. It has also been reported that physical contact between small, hot particles and larger, relatively cool particles aids in avoiding overheating. This effect is attributed to the minor role of thermal conduction and convective heat transfer between particles.

The particle surface of a healthy reactor wall is constantly renewed, which is largely determined by the particle residence time. If the particle residence time at the wall is short, then kinetic energy is high and a small adiabatic temperature rise is observed. Thus, fluctuations in heat-flux measurements indicate the degree of particle mixing or residence time at the reactor wall. Noteworthy, steady-state conditions for an individual particle is rapid and occurs within 0.1 seconds or less. Short residence times produce high heat-transfer coefficients and lower temperatures at the wall. As layers of particles accrete to form polymer sheets, the heat-transfer coefficient decreases. Consequently, excess temperatures result in particle fusion and melting, thereby producing polymer sheets. Following this, disruption in fluidization patterns is generally evident, such as, for example, catalyst feed interruption, plugging of the product discharge system, and the occurrence of the sheets (fused agglomerates) in the product.

Maintaining constant and consistent fluidization in a reactor is critical to high throughout. Fluidized bulk density measurements indicate bed-level oscillations, bubbles and slugs. Slugs may also be formed due to the coalescence of bubbles, in particular where there is a high gas/solid ratio. As pressure decreases, the existing gas expands and forms bubbles. Bubbles of gas increase in size and then coalesce to form gas plugs that separate the solid emulsion phase into slugs. The occurrence of slug flow leads to large variations in mass-flow-rates and a decrease in pressure in the reactor. The large amplitude waves move at a velocity less than the mixture velocity.

U.S. Pat. No. 5,148,405, which is incorporated herein by reference, describes the use of acoustic emission to measure slug flow in a multiphase flow pipeline. In a pipeline, disruptions in flow result from gravitational forces, thereby causing stratified unstable waves to grow on the gas/liquid interface that eventually bridge a pipe and form slugs.

Many advantages are afforded by acoustic emissions measurements, namely, real-time information and quantitative and qualitative process control. Acoustic emission is a non-invasive technique that involves either active or passive detection to measure energy in the form of vibrational waves. In general, acoustics refer to the generation, transmission and reception of energy, which can pass through gases, liquids and solids.

Pressure in a reactor is often monitored to indicate indirectly the state of fluidization in the system as a whole by detecting bed-flow oscillations. Pressure differentials are commonly measured with pressure taps. Pressure differentials provide a qualitative measure of the reactor operability and, thus, do not predict or allow prevention of major continuity disturbances. An analysis technique that functions on-line in a manner such that precursors of sheeting states are identified in real-time has not been described.

Because many variables in a reactor system effect non-linear response, use of non-linear models to control the chemical processes resulting in such non-linear effects are recognized in the art. For example, U.S. Pat. No. 6,263,355, which is incorporated herein by reference, describes a rapid noise filter that minimizes spurious control events by removing noise in a sensor or controller output signal. U.S. Pat. No. 6,122,557, which is incorporated herein by reference, teaches a method for controlling a chemical reactor, preferably the pressure, using a feed-forward subroutine for calculating parametric balances responsive to multivariable inputs which takes advantage of a rapid noise filtering subroutine.

The present invention employs non-linear analytical models derived from a continuous reactor in determining the onset and presence of sheeting. Thus, the present invention provides a cost effective and efficient method to evaluate reactor operation in a fluidized bed reactor in order to control major continuity disturbances in the reactor, in. particular, sheeting events. It is these aspects of evaluation, analysis and control of reactor continuity that are addressed herein.

SUMMARY OF THE INVENTION

The present invention provides a method of evaluating a commercial gas-phase fluid bed reactor continuity by measuring at least one system variable, filtering the data to demodulate a time series and calculating a signal, which is indicative of reactor continuity. System variables comprise an acoustic emission, a differential pressure, a bed total weight/volume, a fluidized bulk density, a static voltage and a reactor wall temperature.

Further, the present invention provides a method of determining reactor continuity by measuring acoustic transmission, filtering the transmission data and calculating a signal that determines a precursor state of sheeting, a change in fluidization or a fluidization transition state.

The invention also provides a method of controlling reactor continuity in a gas-phase fluid bed reactor comprising measuring at least one system variable over time, filtering the data set to demodulate a time series and calculating a signal from the filtered data. The reactor continuity is determined by comparing the calculated signal for the reactor to a signal of a control reactor and, if necessary, is controlled by applying a counter measure and such determinations and/or control by the application of counter measure can be a performed locally or remotely using well-known effective communications and connectivity technologies.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF SUMMARY OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
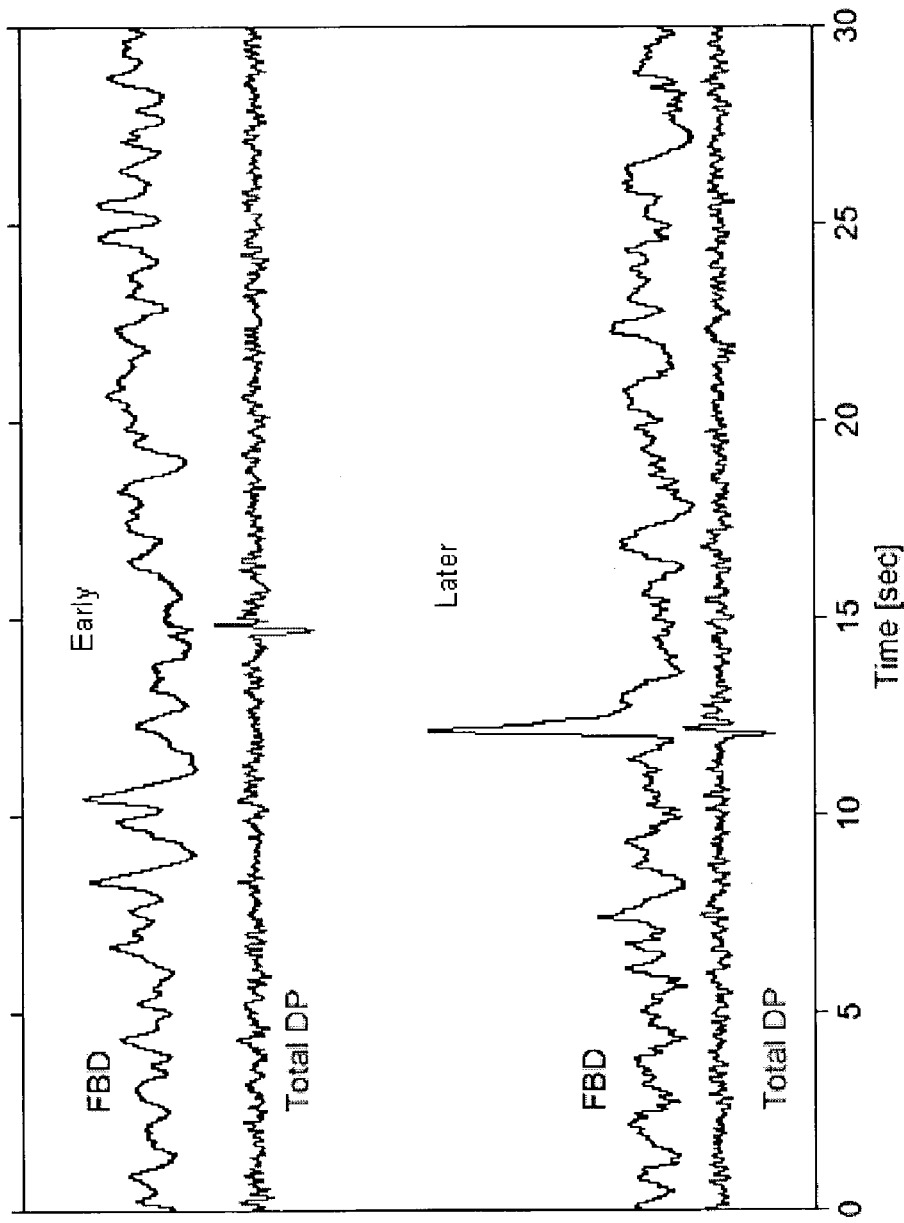
FIG. 1. Time-series illustrating the effects of the discharge spikes on the fluidized bulk density measurement data.

As used herein the specification, "a" or "an" may mean one or more. As used herein in the claim(s), when used in conjunction with the word "comprising", the words "a" or "an" may mean one or more than one. As used herein "another" may mean at least a second or more. By "locally" as used herein reference to reactor continuity determinations and controlling with counter measures, it is meant with the battery limits of the polymerization plant comprising the reactor and post-reactor process system. By "remotely" as used herein reference to reactor continuity determinations and controlling with counter measures, it is meant outside the battery limits of the polymerization plant comprising the reactor and post-reactor process system, including greater distances such as, for example, with centralized determinations and control being located in the United States of America for a polymerization plant located in southern hemisphere.

Optimal reactor continuity is preferred and refers to a steady and efficient operation of a gas-phase fluidized bed reactor. The continuity results from the cumulative effects of system variables such as fluidized bulk density, reactor and reactor wall temperature, static voltage, bed volume and bed pressure. A disturbance in the reactor continuity adversely effects production. A major disturbance is characterized by, for example, sheeting which refers to the formation or agglomeration of polymer sheets on a reactor wall or dome (see U.S. Pat. Nos. 5,436,304 and 5,405,922). Generally, major sheeting events require a reactor shutdown to correct. The invention relates to monitoring, detecting, analyzing, and controlling the reactor continuity during reaction initiation, nascent growth of the polymer, and termination of polymerization.

In one embodiment, the present invention provides a method of determining reactor continuity comprising the steps of measuring at least one system variable of the reactor during a time period to generate data, filtering the data to demodulate a time series, calculating a signal from the filtered data and determining the reactor continuity by comparing the calculated signal to a signal of a control reactor.

In a specific embodiment the time period comprises a time required to collect more than one data point. In a specific embodiment, the system variable includes acoustic emission, a differential bed pressure, a bed total weight/volume, a fluidized bulk density, a static voltage and a reactor wall temperature.

The data preferably comprises high speed data that is obtained at a collection rate greater than 1 Hz. This includes measurements recorded, at least, at 10 data points per second for a duration of 1–60 minutes. The data acquisition process is iterative at a range of collection rates from minutes to hourly intervals. This high speed data is low passed filtered with a cutoff frequency of about 40 Hz, thus, frequency content above 40 Hz, or any event shorter than 25 msec in duration, is attenuated. Data recorded at about 1 point per second continuously throughout a test span are considered low speed data. A skilled artisan recognizes that data collection rates vary with experimental conditions, and the rate employed is sufficient to detect reactor continuity. A skilled artisan is aware that the appropriate instruments used to obtain data (i.e., bed pressure is measured by using a pressure tap) are well known in the art.

In a preferred specific embodiment, the high speed data comprises a filtered fluidized bulk density, a bed total pressure drop, a static voltage, an acoustic emission and a skin thermocouple measurement. A skilled artisan is aware that the appropriate instruments used to obtain data are commercially available.

In a specific embodiment, the calculated signal comprises entropy, which demonstrates a shift, preferably a decrease, in the calculated signal as a result of a disturbance in reactor continuity.

In another specific embodiment, the calculated signal comprises a cycle time, which demonstrates a significant change, preferably an increase, in the calculated signal as a result of a continuity disturbance. By the phrase "cycle time" is meant the average residence time of particles at the reactor wall and is a function of bubble generation and fluidization characteristics. Cycle time is derived from data obtained from measuring at least one system variable that indicates reactor continuity, such as fluidized bulk density and reactor wall temperature.

In alternative specific embodiment, the signal comprises a mean deviation. The terms "mean deviation", "average absolute deviation" and "mean absolute deviation" are used interchangeably. The mean deviation (MD) is used as a measure of the magnitude of signal fluctuation, determined by the following equation (EQU. 1)

$$MD = <|x_i - \bar{x}|>, \quad (1)$$

In this sense, MD is like standard deviation or variance where $x_i$ is the measurement at index i, $\bar{x}$ is the data mean. Here, |•| signifies the absolute value, and <·>, signifies the expected value (when the operation $|x_i - \bar{x}|$ is averaged over the entire time series).

In another specific embodiment, the reactor continuity determined by the method of the present invention comprises a precursor state of sheeting, a change in fluidization, and a fluidization transition state.

An alternative embodiment further comprises determining the reactor continuity by comparing a cycle time for the reactor to a mean deviation of the same reactor, wherein an increase in the cycle time and a concomitant decrease in the mean deviation indicates a decrease in reactor continuity, and specifically the presence of sheeting.

Another specific embodiment provides for filtering the data comprising a low pass filter, including a wavelet dyadic filter, a Clapp-Hively filter and a root mean square. Preferably, the filter demodulates the time series to produce distinctive indications of reactor continuity.

In another embodiment, the invention provides a method of determining a reactor continuity comprising the steps of applying an acoustic emission sensor to a reactor wall, measuring an acoustic transmission to generate data, filtering the data to demodulate a time series, calculating a signal for the time series and determining the reactor continuity by comparing the calculated signal to a signal of a control reactor. One skilled in the art recognizes that calculated signal from a first time series is a suitable control reactor for comparison of a calculated signal from a second time series of the same reactor. In this instance, an alteration in the calculated signal of the second time series as compared with the calculated signal of a first times series indicates an altered reactor continuity.

In a specific embodiment, the acoustic emission is measured in the range of about 100 kHz to 400 kHz and preferably 190 kHz. In a further specific embodiment, the acoustic emission is measured with a passive acoustic emission detector although an active acoustic emission detector is also contemplated.

In a specific embodiment, the data is filtered comprising a low pass filter such as, for example, a Clapp-Hively filter, a wavelet filter, or by extracting a root mean square.

In another specific embodiment, the calculated signal includes an entropy, a cycle time, a mean deviation, a correlation dimension, power spectrum, and an eigenvalue spectrum. The latter is generated, for example, by applying a principal component analysis.

In a specific embodiment, determining the reactor continuity includes determining a precursor state of sheeting, a change in fluidization and/or a fluidization transition state.

In yet another embodiment is a method of controlling reactor continuity in a gas-phase fluid bed reactor comprising the steps of measuring at least one system variable of the reactor during a time period to generate data, filtering the data to demodulate a time series, calculating a signal from the filtered data, determining the reactor continuity by comparing the calculated signal for the reactor to a calculated signal of a control reactor and applying a counter measure to control reactor.

In a specific embodiment, the system variable comprises an acoustic emission, a differential pressure, a bed total weight/volume, a fluidized bulk density, a static voltage and a reactor wall temperature. In a further specific embodiment, the acoustic emission is measured with a passive acoustic emission detector.

In a preferred specific embodiment, the data set comprises high speed data that includes a filtered fluidized bulk density, a bed total pressure drop, a static voltage, an acoustic emission and a skin thermocouple measurement.

In a specific embodiment of the present invention, the calculated signal comprises a signal entropy, a cycle time and a mean deviation. In calculating a signal, a cycle time is preferred, but is not limited to, data that is nonstationary (i.e., fluidized bulk density). The entropy is a measure of signal complexity such that a decrease in entropy suggests a decrease in mixing, a decrease in reactor continuity and excess polymer formation on and/or near the reactor wall.

In a specific embodiment, the counter measure comprises injecting a poison into the reactor, which includes, for example, carbon monoxide, carbon dioxide, oxygen, and water. In another specific embodiment, the counter measure comprises adding anti-static and pro-static agents (see U.S. Pat. Nos. 4,803,251 and 5,391,657, which are incorporated herein by reference).

In yet other specific embodiments, the counter measure comprises adjusting a temperature of the reactor, adjusting a velocity of a medium, adding a reactor surface modifier, such as aluminum distearate, and adding a gas pulse. In an embodiment in which a gas pulse is added as a counter measure, the gas pulse is preferably iterative and added until a desired reactor continuity and/or operability is achieved.

In further specific embodiments, the counter measure comprises adjustments to monomer partial pressure, to reactor bed level, to catalyst feed rate, and to ethylene feed rate.

In an alternative embodiment, the method further comprises determining reactor continuity by comparing a cycle time for the reactor to a mean deviation of the reactor.

The reactor wall temperature is a system variable readily measured with skin-thermocouples. These signals experience long-time-scale drifts in local mean, perhaps associated with "cold cells" in the reactor dynamics. Although these drifts contain some information of interest, they create problems for some numerical algorithms. To reduce the drifts, the Clapp-Hively filter, a wavelet filter or a root mean square of the data is employed. The Clapp-Hively filter is a zero-phase-shift, second-order polynomial fit, and it demodulates the signal into low and high pass bands. For example, a first data point represents a vertex of a parabola in the filtered data. This is computed by applying a least-square fit comprising two data points preceding the first data point and two points succeeding the first data point. The effect of the filter is to separate the time series into low and high pass bands. The filter window width (the number of preceding and succeeding points used in the polynomial fit) determines the break frequency of the filter. Because the window is symmetric, the filter has zero phase shift.

Figure 2:
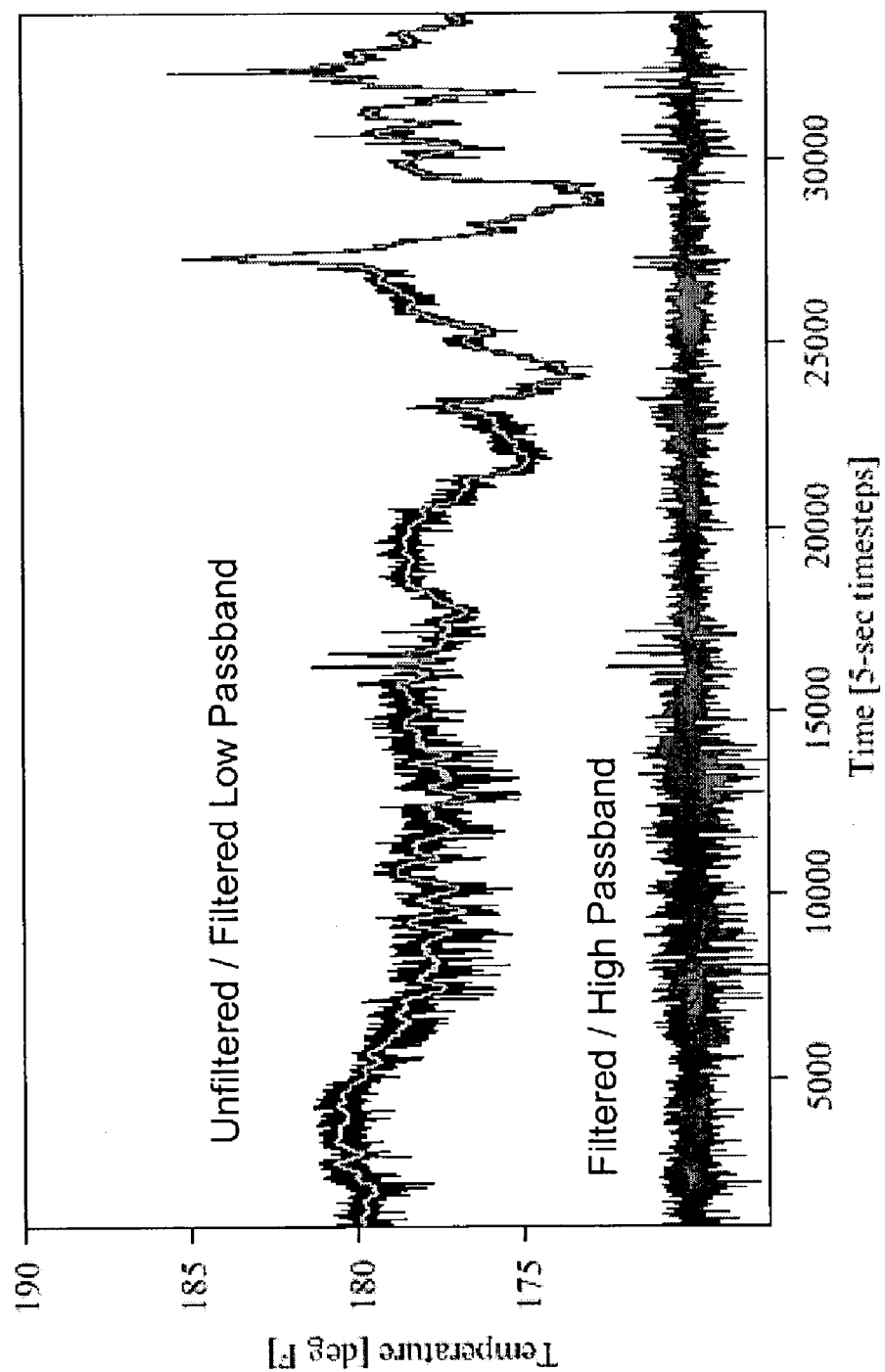
FIG. 2. Illustration depicting filtering skin-thermocouple measurements.

An illustration of how the filter works on skin-thermocouple measurements is shown in FIG. 2. The unfiltered time series is the top signal. Superimposed on the unfiltered signal is the low-passband time series, which is coincidental on the unfiltered signal, and the high-passband time series, which is the bottom signal. The low passband contains the nuisance signal, the slow drift in the signal mean, and the high passband contains the selected dynamics of interest.

Figure 3:
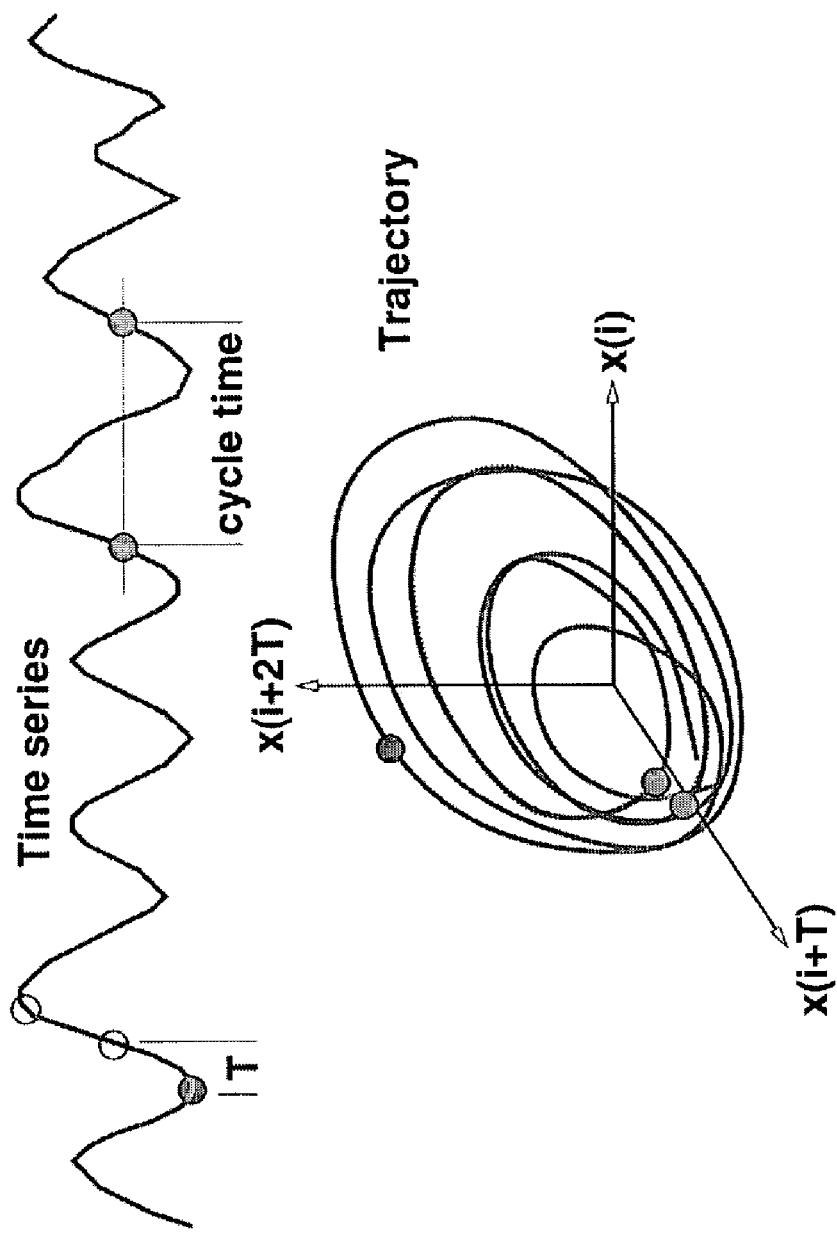
FIG. 3. Illustration of delay-coordinate embedding and the relationship of the intercrossing interval with a phase-space orbit.

The average cycle time is the time-averaged duration for a signal's reconstructed phase-space trajectory to traverse an orbit. Practically, this value is estimated using a form of Poincaré sectioning based on successive directional crossings of a defined threshold. FIG. 3 outlines the process of delay-coordinate embedding and the relationship of the intercrossing interval with a phase-space orbit. The time series is "embedded" by taking several (here, three) successive measurements, each separated by embedding delay T. By plotting these (three) points for a sliding temporal index i, the trajectory is obtained.

A cycle time is calculated by choosing a threshold (the segment defined by gray-circle points at the perimeter in the time series) and by measuring the interval between successive threshold crossings (the open-circle points and the solid-circle point in the time series); the phase-space orbit is shown as the segment on the trajectory plot beginning and ending with gray-circle points. Delay-coordinate embedding is discussed further by Schouten J. C., Takens F., and van den Bleek C. M. in "Maximum-likelihood estimation of the entrophy of an attractor", *Physical Review E* 49, pp. 126–129 (1994), the disclosure of which is incorporated herein by reference.

The Daw adaptation of the Delft maximum-likelihood estimator of Kolmogorov-Sinai entropy is employed as a measure of signal complexity (see Schouten J. C., Takens F., van den Bleek C. M., "Maximum-likelihood estimation of the entrophy of an attractor", *Physical Review E* 49, pp. 126–129 (1994) and Schouten J. C., van den Bleek C. M., "Monitoring the quality of fluidization using the short-term predictability of pressure fluctuations", *AIChE Journal* 44: 48–60 (1998), which are incorporated herein by reference). Briefly, the estimator $\hat{K}_{ML}$ quantifies the rate at which entropy is generated in the attractor by measuring the time for nearby trajectory segments to diverge. The method relies on a time-scale parameter, the segment length, and a length-scale parameter; the cutoff length. Based on these parameters, a single number is obtained for each measurement time series, and this number is compared over a range of bed operating conditions to correlate signal complexity with a sheeting propensity.

Another measure of signal complexity based on data symbolization is a modified form of Shannon entropy. Symbolization coarse-grains time-series data, and when a symbol series is "embedded" and encoded the frequencies of dynamical patterns are easily catalogued. The symbol-sequence histogram is such a catalog, and its tally is affected by three parameters: the symbol-set size, the sequence length, and the inter-symbol interval. The Shannon entropy is a measure of the degree of organization of the symbol-sequence histogram; in effect, it is a measure of how randomly the time series behaves, given the chosen length and time scales of observation. A modified form of Shannon entropy ($H_{SM}$) is used and is given by where $N_{seq}$ is the number of sequences observed with non-zero frequency and $p_I$ is the observed probability of sequence i. For "random" data, $H_{SM} \approx 1$, for nonrandom data, $0 < H_{SM} < 1$ (Finney C. E. A., Green J. B. Jr., Daw C. S., "Symbolic time-series analysis of engine combustion measurements", *SAE Paper No.* 980624 (1998) and Tang X. Z., Tracy E. R., "Data compression and information retrieval via symbolization", *Chaos* 8, pp. 688–696 (1998), the disclosures of which are incorporated herein by reference).

Acoustic emission is employed to compare interference patterns or changes in fluidization patterns of a reactor to evaluate reactor continuity, preferably by determining the presence of or predicting the onset of sheeting. An acoustic emission transducer is used to apply the ultrasonic frequency to the reactor wall at positions that either are vulnerable to sheeting occurrences or are not vulnerable to sheeting occurrences. Detection of an ultrasonic sound pattern, also known as an acoustic emission, is measured by active or passive sonar detectors. A skilled artisan is aware that ultrasonic frequency ranges refer to frequencies from about 20 kHz to about 1 MHz although no well-defined upper limit is recognized. In the instant case, 190 kHz is used but one of ordinary skill in the art is able to envision other ultrasonic frequencies to produce sound patterns indicative of the reactor continuity. Specifically, in a fluid-bed, acoustic emissions from particle impacts at or near the reactor wall are measured and include, but are not limited to, particle-wall interactions and particle-particle interactions.

In the case of a fluid-bed, emissions from particle impacts at or near the reactor wall are measured by "hearing" particle-wall and particle-particle contacts. By detecting only those frequencies in the ultrasonic frequency range the measured emissions consist primarily of those transmitted through the reactor wall. In this way the background noise that would be transmitted through air would not be detected at the ultrasonic frequencies, thereby increasing the signal-to-noise ratio.

The acoustic emission (AE) is measured as transmission which refers to the transfer of energy in the form of regular mechanical vibration through a solid, liquid or gaseous medium. A skilled artisan is aware that acoustic transmission depends on the displacement of individual molecules. Applying a burst of acoustic energy effects an oscillation in accordance with the frequency pattern of the displacement. An acoustic transducer converts these oscillations or disturbances in the natural random motion of individual molecules into electrical impulses. In the instant case, an AC signal is converted to DC via an RMS conversion using the following equation (EQU. 2):

$$\text{RMS of AE} = A^2 = G_0 m \rho_f v_n^3 \qquad (2)$$

Her n represents the number of samples in the sampling period and $x_i$ is the data point value at time i. If necessary the analogue electrical signal is amplified by use of a preamplifier. This provides the output capable of driving the signal over long distances. The transducer is suitably placed in direct contact with the external reactor wall. To ensure a good acoustic coupling between the transducer and the metal surface silicon grease or other suitable material may be used. A steady, but higher than background, level is observed as the body of the gas bubble passes, and then the signal finally decreases to the background level following the rear of the bubble. Such a characteristic trace is associated with the turbulence energy of the different parts of the bubble. Any events which consist of a variation in the local gas or liquid flow rates may be detected as a change in the signal level. Such events may be observed, for example, as alterations in signal level.

As described herein, non-linear analysis, also referred to as chaos analysis, allows detection of fluidization changes in a polyethylene reactor, detection of sheeting, and identifies sheeting precursors. A model relationship is used to establish a physical concept between sheeting and process measurements. Within the scope of this invention is a diagnostic method using non-linear analysis to determine reactor continuity, and specifically, determine the onset and/or presence of sheeting, thereby reducing the negative impact of sheeting on reactor operability.

EXAMPLES

The following examples are included to demonstrate preferred embodiments of the invention. It should be appreciated by those skilled in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Data-set Definitions

High-speed data consisted of filtered fluidized bulk density, bed total pressure drop, static voltage, skin thermocouple and acoustic emission. The high-speed measurements were typically recorded at 200 samples per second for a duration of five minutes once per hour; the 1999–11 data were recorded at more frequent intervals. Before being sampled and recorded, the transducer signals for the bulk density, total bed weight, static and acoustic emission were analog low-pass filtered with a cutoff frequency of 40 Hz, so that frequency content above 40 Hz, or any event shorter than 25 msec in duration, was attenuated. The skin thermocouple data were decimated by a factor of 10 and low-pass filtered using a simple RC filter with a cutoff frequency of 5 Hz.

Low-speed data consisted of skin thermocouple, reactor static and bed pressure and temperature. The low-speed measurements were recorded at 5 samples per second continuously throughout the test span.

Acoustic emission data was acquired using commercially available transducers (Process Analysis & Automation) with an applied frequency of 190 kHz. The transducers were located at several positions on the external reactor wall: distributor plate, reaction zone, transition side of the dome, and the recycle line.

Example 2

Data Selection for Non-linear Analysis

This process involved evaluating the completeness of the data record, specifically regarding relationship to known sheeting incidents, and evaluating the integrity of the data through analytical means. Data was excluded only if a massive sheeting incident occurred and the reactor required shut down. Glitches in the measurement signals that disqualified data from further analysis included visible nonstationarity (slow drift in mean), sharp amplitude changes, and signal saturation or overdiscretization. Additionally, data taken during logged process transients were excluded from analysis to avoid spurious identification of signal changes unrelated to natural transition to sheeting. Other process artifacts, specifically sharp pressure changes during product discharge, were identified to exclude these anomalies from analysis. In the later part of the data series, the FBD measurements contain strong spikes associated with product discharges, whereas in the earlier series, such spikes are barely visible, if at all. The reason for these differences is unknown. FIG. 1 illustrates the effects of the discharge spikes on the FBD measurement data.

Data analyzed incorporated a wide range of operating conditions including a marked presence of sheeting events. These data and their labels are "SAMPLE 1"("unstable"), "SAMPLE 2" ("transition" or "intermediate") and "SAMPLE 3" ("stable"), where the stability label refers to propensity for sheeting.

The low-speed skin-thermocouple measurements generally contain very long time-scale mean shifts (possibly evidence of "cold cells", local areas of lower temperature because of reduced reaction rates) and some degree of discretization. Because of their value in indicating sheeting events, none of the thermocouple signals was rejected, but all were detrended to remove the long-term drift before analysis. Because most tests in time-series analysis presume stationarity, verification of stationarity was the next step in identifying data suitable for further analysis.

Stationarity implies that certain statistical measures of a time series do not change over time. The Kennel phase-space stationarity test was employed to test for stationarity (see Kennel M. B, "Statistical test for dynamical nonstationarity in observed time-series data", *Physical Review E*

56, pp. 316–321 (1997), the disclosure of which is incorporated herein by reference). This test evaluates whether similar time-series patterns are evenly distributed over time, or whether these patterns are biased to a certain location in the time series. The Kennel test has been employed extensively in previous work with PE-bed pressure data (see Kennel M. B, "Statistical test for dynamical nonstationarity in observed time-series data", *Physical Review E* 56, pp. 316–321 (1997), the disclosure of which is incorporated herein by reference).

Example 3

Cycle Time Analysis

Cycle time data filtered using a Daubechies second order wavelet indicated that sheeting is predicted within 5–12 minutes with average of 7.5 minutes warning. The cycle time was characteristic for each catalyst type and indicative of the resin residence time at the reactor wall. Based on this, residence times of 2–5 minutes stagnation seem to result in sheeting. Sheeting residence times agree with calculations of thermal runaway. Applying a counter measure such as short, iterative pulses of $H_2$, changing the velocity of the medium, injecting poisons such as $CO_2$, CO, oxygen or water, antistatic or pro-static agents, adjusting the temperature of the reactor, altering the monomer partial pressure, reactor bed level, catalyst feed rate, and ethylene feed rate present viable mechanisms to control the reactor continuity.

Example 4

Fluidized Bulk Density (FBD) Measurements

Because the FBD measurement series tended to be moderately to strongly nonstationary, complexity measures were eschewed in favor of the average cycle time, which was expected to be less adversely affected by nonstationarity.

Figure 4:
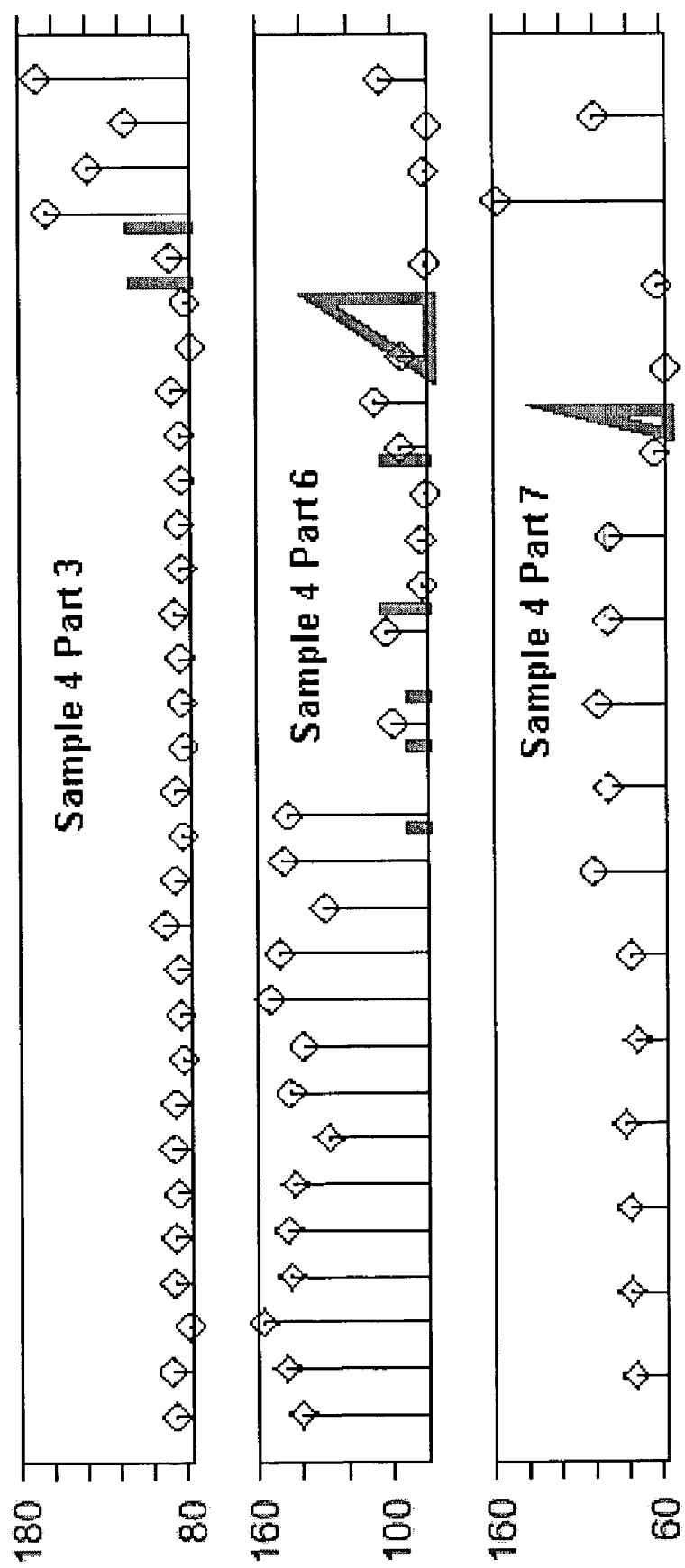
FIG. 4. Cycle times calculated from thermocouple measurements indicate sheeting incidents.

In three data series, "SAMPLE 4" parts 3, 6, and 7, the average cycle times of the FBD time series shifted dramatically before or near indications of sheeting, as seen in the skin-thermocouple measurements. FIG. 4 shows the average cycle times (plotted with ◊ symbols), recorded at hourly intervals; the abscissa is time in hours the ordinate is time in 5 msec timesteps (200=1 sec). The sheeting incidents, identified from large, sharp excursions in the thermocouple signals, are plotted either as red bars (for very brief spikes) or red triangles (for protracted excursions). In parts 3 and 8, there may be significant decreases in cycle times between 20 to 60 minutes preceding the skin-thermocouple events. The data suggests that a sheeting precursor state is observed and quantified.

Figure 10:
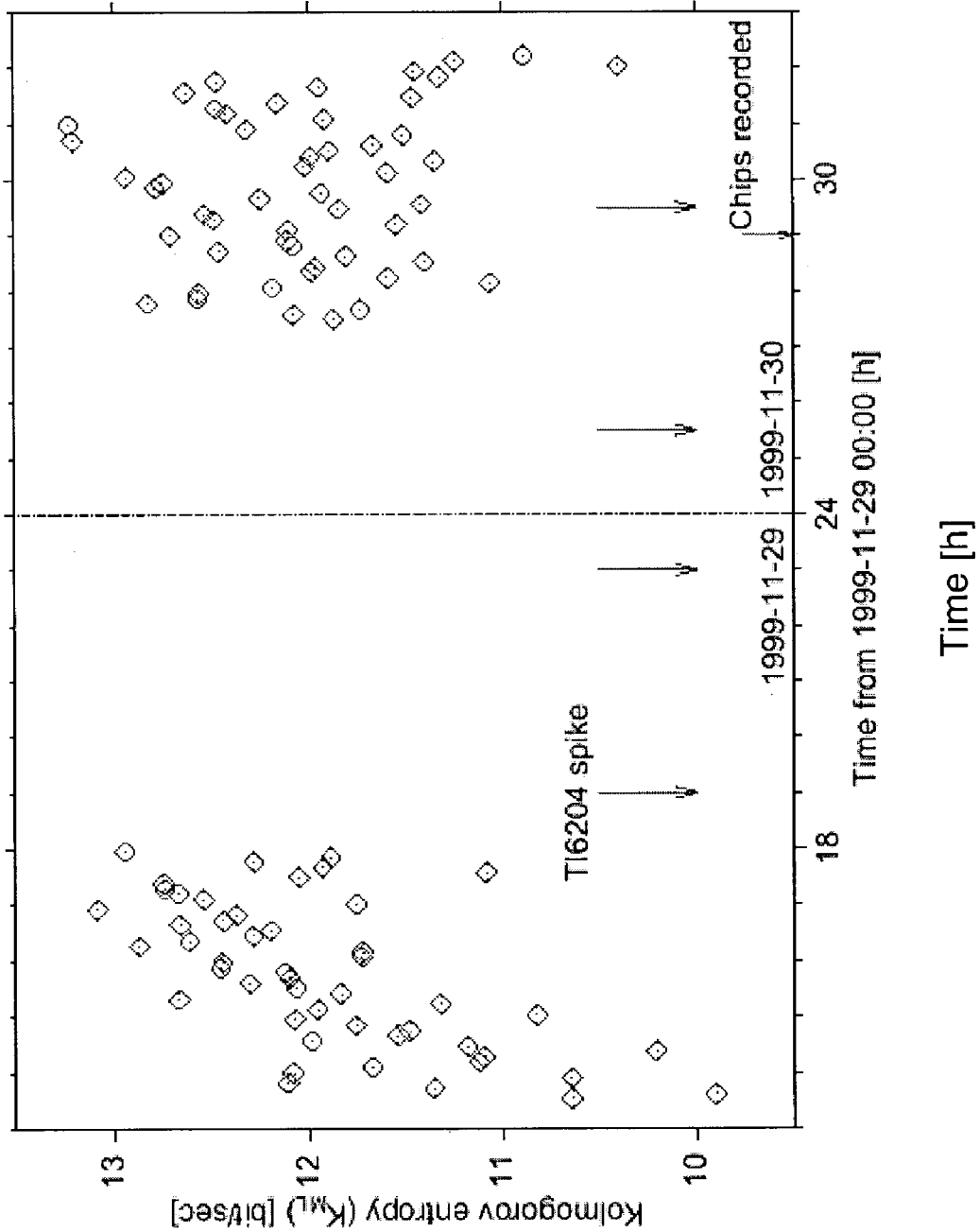
FIG. 10. Kolmogorov entropy signal calculated from filtered fluidized bulk density measurements.

A second set of FBD data were based on runs to produce several very low density (VLDPE) samples using "SAMPLE 2" catalyst. Several process changes occurred before 12:30, and at 13:00 some lower-bed TI activity was observed. In period between 13:23 and 18:00, the FBD signal complexity, as quantified by the Kolmogorov entropy, steadily increased, as seen in FIG. 10. Within an hour of the beginning of the data gap, a temperature excursion was visible (with sensor TI6204). The steady rise in Kolmogorov entropy was matched by a steady decrease in cycle times. The observed trends in this later FBD data are consistent with those observed in the previously analyzed FBD data.

Example 5

Entropy, Mean Deviation and Cycle Time

Figure 5:
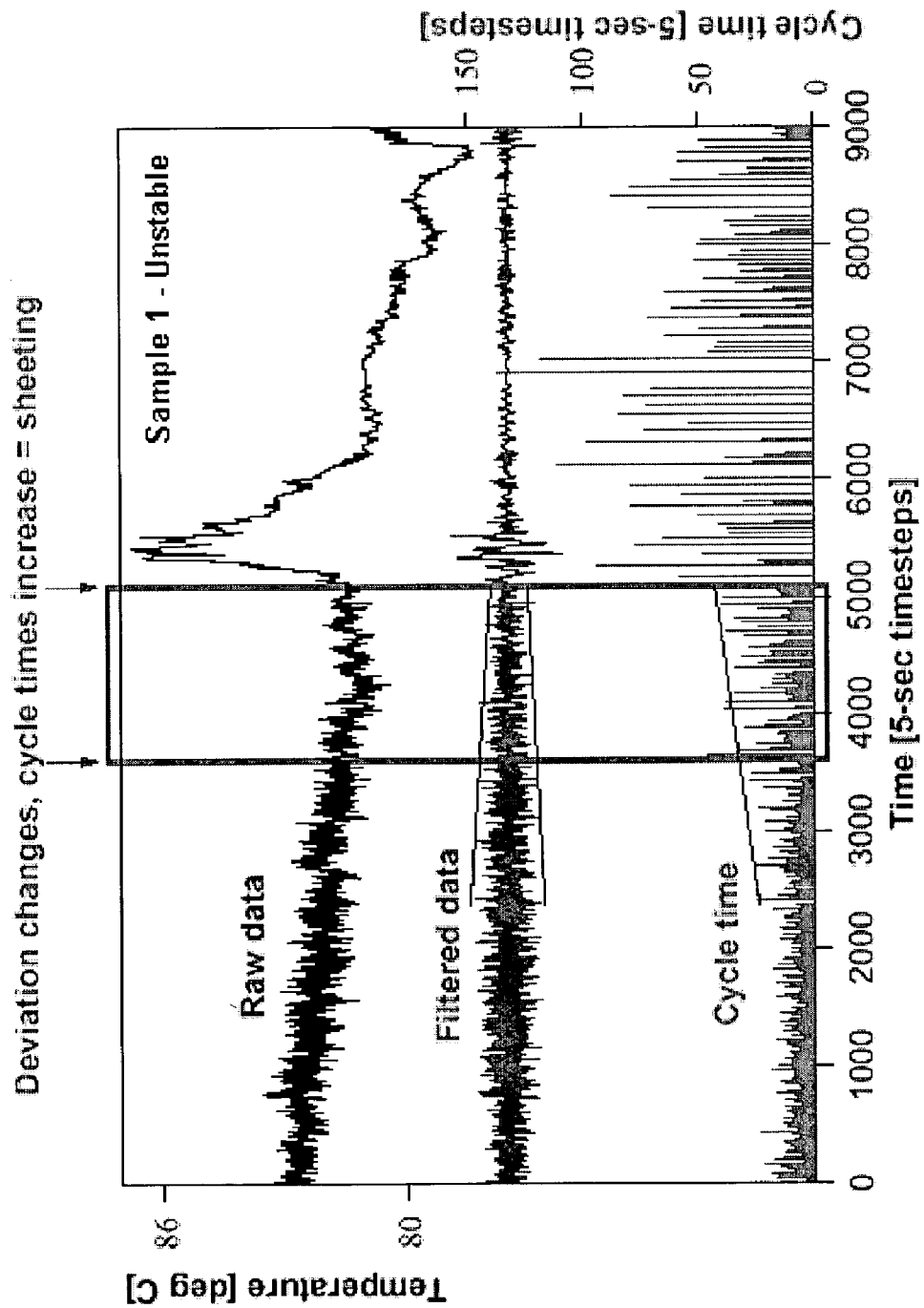
FIG. 5. Mean deviation and cycle time of an unstable reactor.

A significant correlation between the mean deviation and average cycle times and the propensity to sheet was observed. For the "unstable" case (FIG. 5), mean deviation decreases and cycle times increase preceding sheeting. As suggested by the guide lines, as a general trend preceding the massive sheeting incident, the mean deviation steadily decreases and the cycle times increase up to the sheeting event. After the temperature excursion, the temperature fluctuations become longer in duration, suggesting disruption of mixing at the reactor wall.

Figure 6:
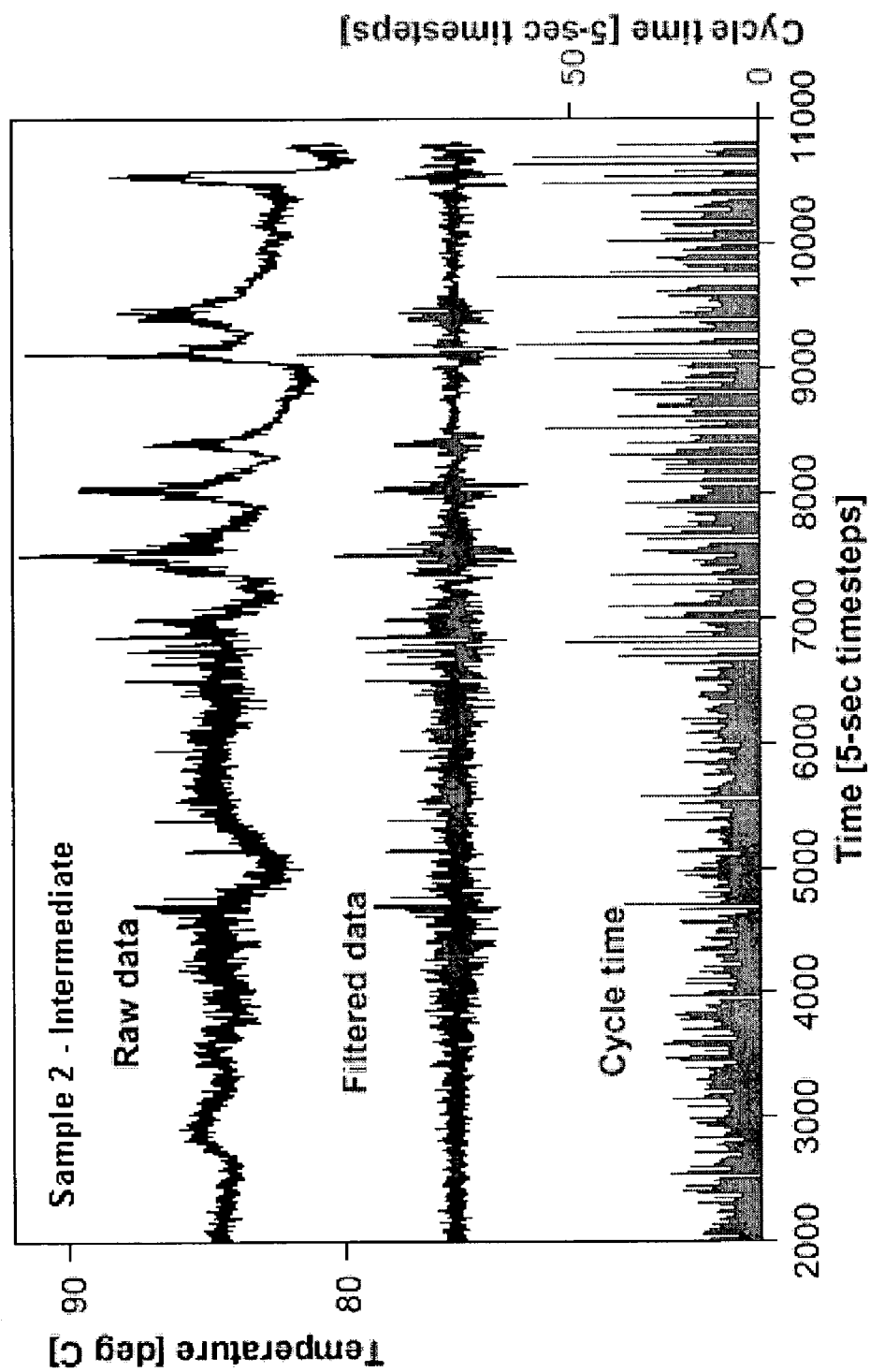
FIG. 6. Mean deviation and cycle time of an intermediate reactor.

For the "intermediate" case (FIG. 6) some of the above-mentioned trends are observed. At about index 5000, there is a process change resulting in a dip in the raw data related to the point where the reactor shifted from condensed-mode operation. At about index 6700, cycle times increase, corresponding to the flare-ups seen in the raw and filtered data. Although increases in cycle times agree with the "unstable" case, the mean deviation does not behave similarly, at least in a readily visible manner.

Figure 7:
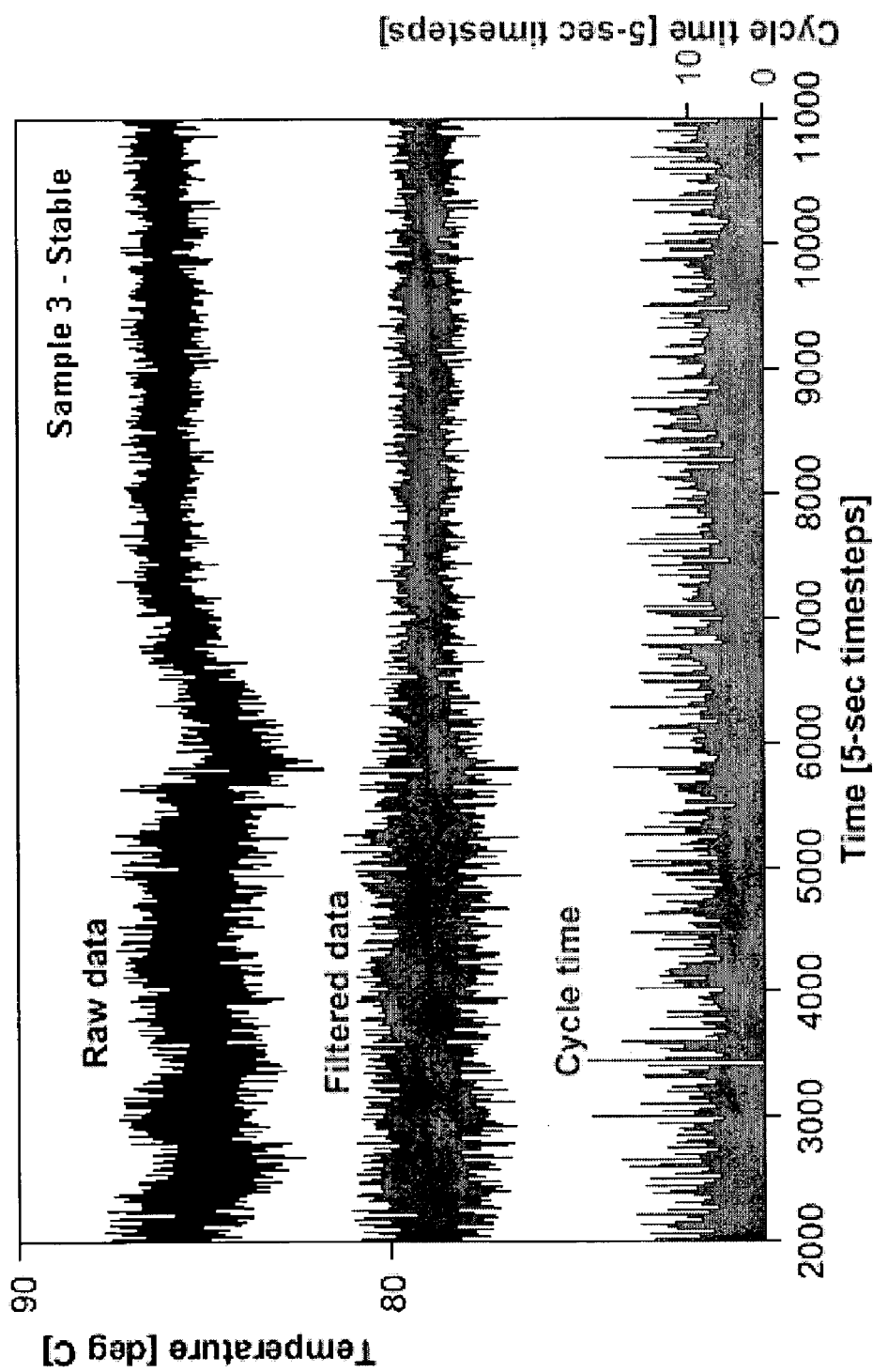
FIG. 7. Mean deviation and cycle time of a stable reactor.

For the "stable" case (FIG. 7), changes in mean deviation and cycle times are related solely to process changes. In FIG. 7, at about index 5800, there is a process change, resulting in a brief decrease in the mean of the raw data. In the corresponding filtered data, the mean deviation decreases after the process change and remains constant thereafter. The cycle times slightly decrease after the process change. There were no known sheeting incidents in this data set.

Figure 8:
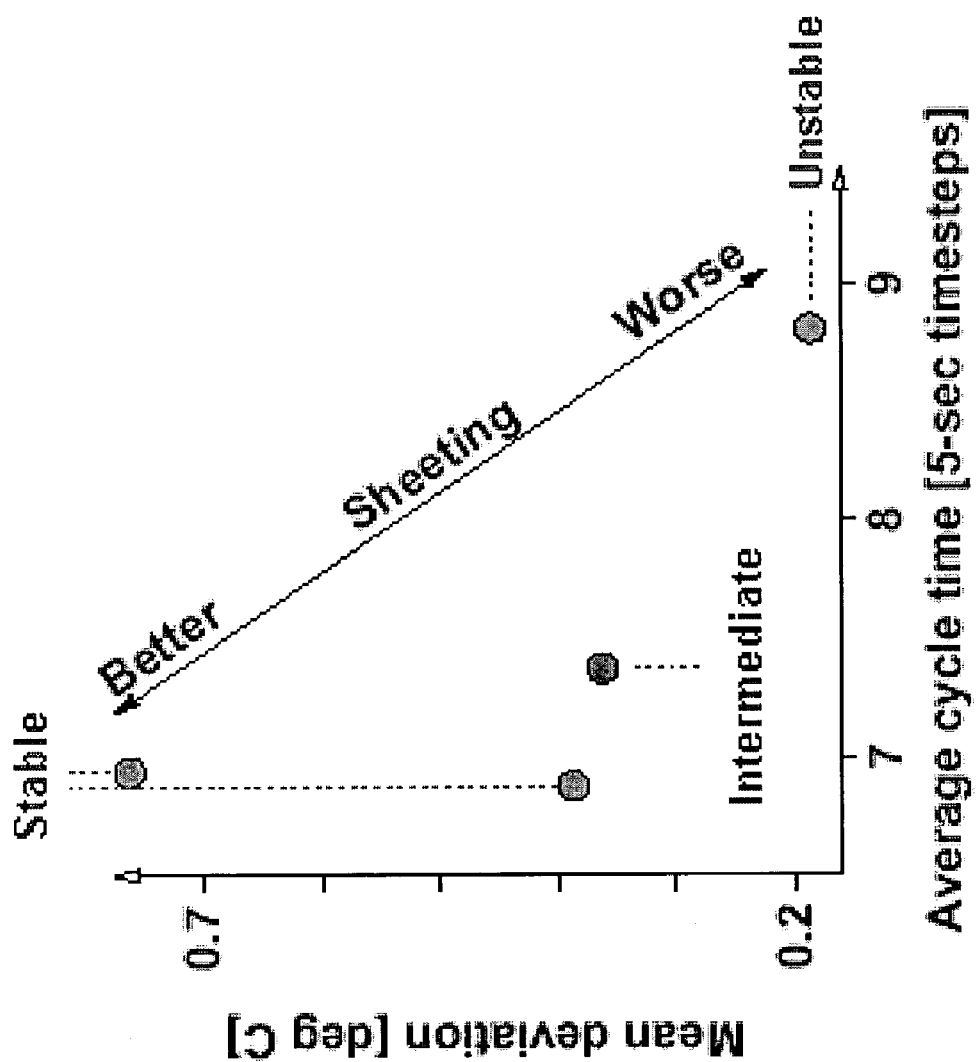
FIG. 8. Correlation between mean deviation, average cycle time and the propensity for different grades to sheet.

There is a correlation between mean deviation, average cycle time and the propensity for different grades to sheet. This correlation is depicted in FIG. 8. In computing the mean deviation and average cycle times, data following process changes and preceding sheeting incidents were used to ensure that the stable behavior of each grade is characterized. The two points for the stable grade correspond to behavior before and after the process changes observed. The reactor demonstrating the worst sheeting occurrence ("SAMPLE 1") produced the longest cycle times and lowest mean deviations suggesting that these characteristics are related to mixing at the reactor wall.

Figure 9:
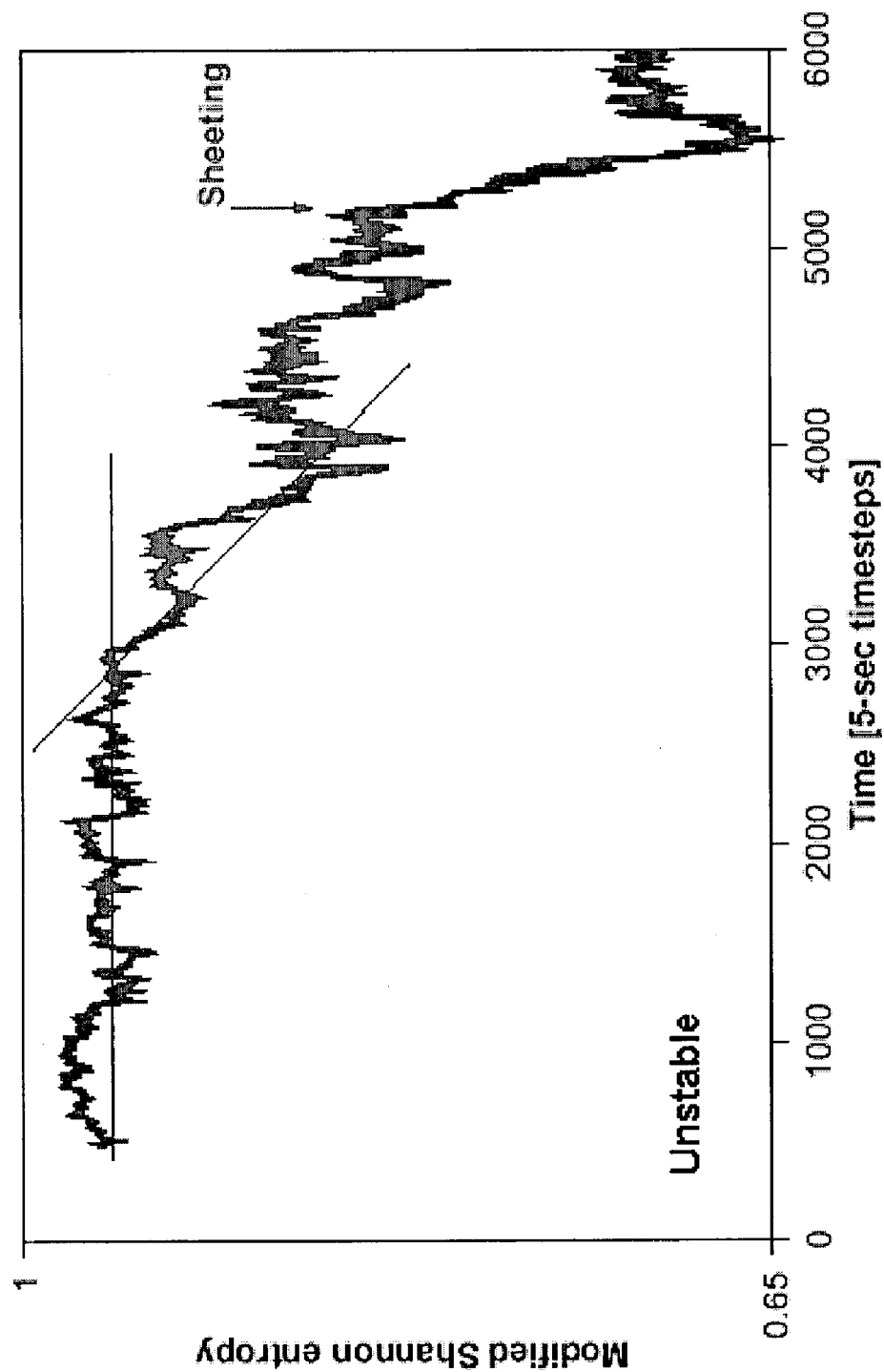
FIG. 9. Symbolization-based Shannon entropy of an unstable reactor.

The symbolization-based Shannon entropy also has distinct trends leading up to sheeting, as seen in FIG. 9 for the "unstable" case. During the period of stable operation (approximately indices 500 to 3000), entropy is relatively constant. At about index 3000, coincidental with the mean deviation and cycle-time trend shifts, entropy unambiguously decreases, indicating a decrease in signal complexity. This decrease in complexity appears to be related to decrease in mixing near the reactor wall.

Example 6

Evaluating Reactor Continuity

The data indicates that trends are evident to determine reactor continuity and specifically the onset or presence of sheeting in the reactor. In both fluidized bulk density and skin-thermocouple measurements, signal time scales shift significantly preceding or during an identified sheeting incident.

Figure 11:
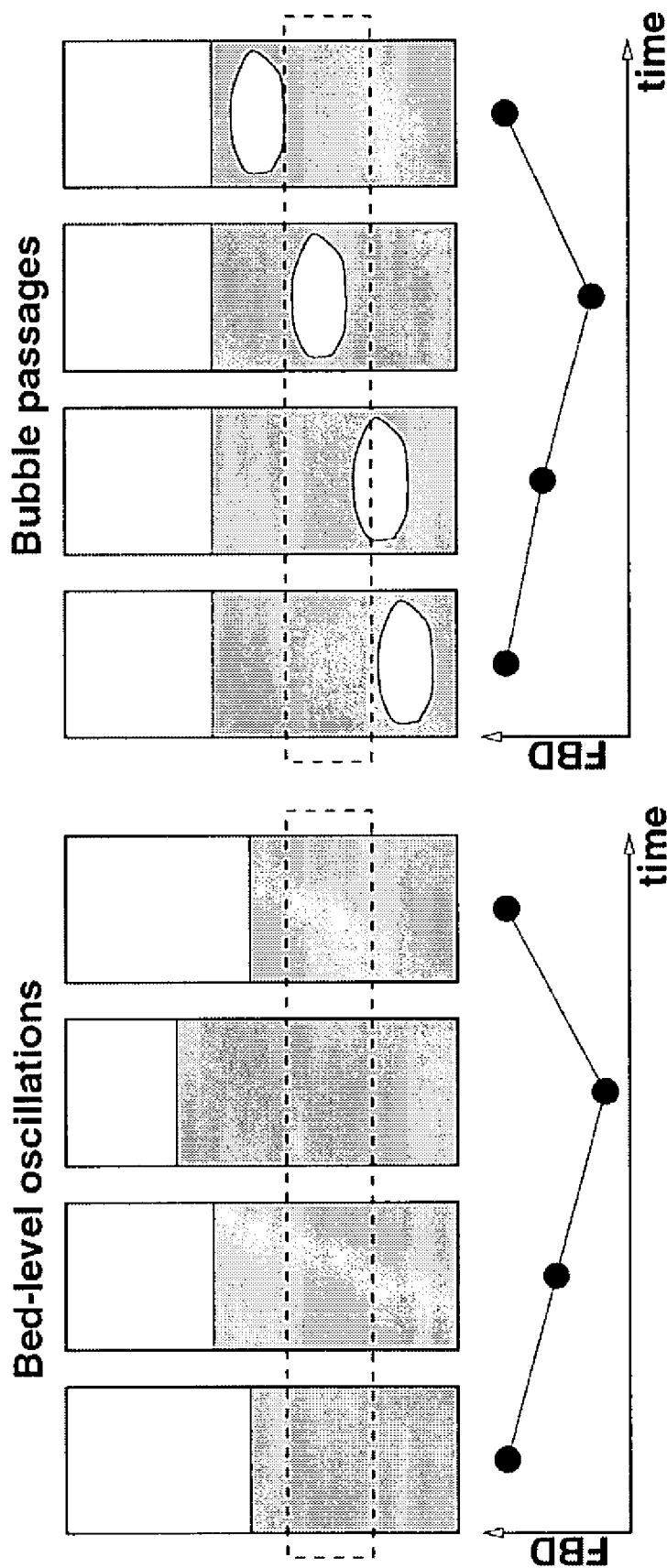
FIG. 11. Relationship of bed oscillations and bubble passages to fluidized bulk density measurement signal.

In the fluidized bulk density measurements, it is conjectured that changes in signal complexity also show up as changes in signal time scales because fluidization patterns shift, either as a result of sheeting or as a pre-state conducive to sheeting. The fluctuations in the FBD measurements are directly related to two processes: bed-level oscillations and bubble passages, as depicted schematically in FIG. 11. Decrease in the average cycle time or increase in the level of complexity probably indicate the increased presence of small bubbles in the reactor, either from nucleation off of agglomerated mass or in mixing patterns which later lead to agglomeration. Generally, it should not be expected that complexity measures and cycle times should be so complementary—the two should be used with equal weight, as each indicates different signal characteristics.

Figure 12:
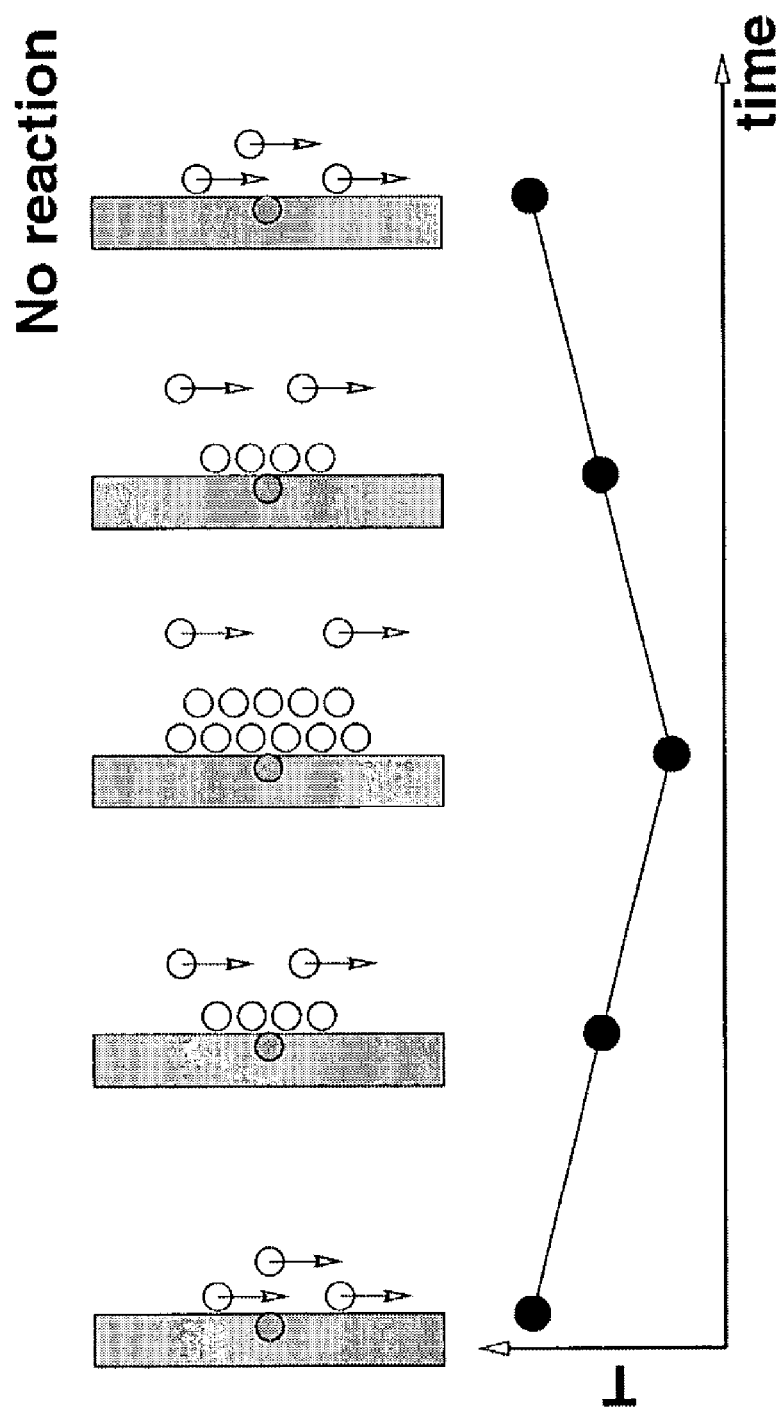
FIG. 12. Effect of particle mixing at or near the reactor wall on a skin thermocouple signal.

Fluctuations in the skin-thermocouple or heat-flux measurements are conjectured to indicate the degree of particle mixing or residence time at the reactor wall. With very short residence times, the heat-transfer coefficient at the wall is high, and temperature is high. As layers of particles accrete, the heat-transfer, coefficient decreases. As these layers are eroded away, the coefficient rise again, and the measured temperature becomes high again. This process is depicted schematically in FIG. 12. The cycle times of thermal signals indicate the degree of activity near the bed wall. It is suggested by the data that the shorter the cycle time, the less propensity to sheet. Long particle residence times indicate insufficient mixing near the bed wall, and hot spots leading to sheeting are then facilitated.

Example 7

Acoustic Emission and Non-Linear Dynamics

Acoustics refer to the generation, transmission and reception of energy in the form of vibrational waves. The acoustic emission of a fluidized bed allows the measurement of particle-particle impacts at or near the wall, including particle-wall impacts. The wall vibrational energy is called "white" noise or acoustical "shot" noise. Acoustic emission is directly related to the granular temperature $T^*$, a fluidization parameter. It is defined as the square fluctuation velocity and measures downward convective flow of particles at the reactor wall. Measuring the acoustic emission of a reactor during a run using a slurry fed catalyst produced characteristic signals for disturbances in reactor continuity prior to a dome sheet dislodging and falling into the bed. In the case of a dry catalyst feed, similar predictive data was observed. A comparison of acoustic emission amplitude to superficial gas velocity indicated a near-linear relationship.

Calculating the Kolmogorov entropy of differential pressure and skin thermocouple data coupled with particle mechanics using a time series embedding and a singular value decomposition indicated that fluidization varies depending on factors such as resin type, anti-foulant level and the state of the distributor plate. Further, precursor sheeting states for dome sheeting were determined as much as 8 hours in advance as was indicated by evaluating more than one system variable. The average absolute deviation or mean deviation calculated on reactors running different catalysts indicated distinct changes in reactor continuity and fluidization in both cases. Similar indications were observed upon calculated cycle times and Kolmogorov entropy of the same data set.

Example 8

Catalyst Transitions

Figure 13:
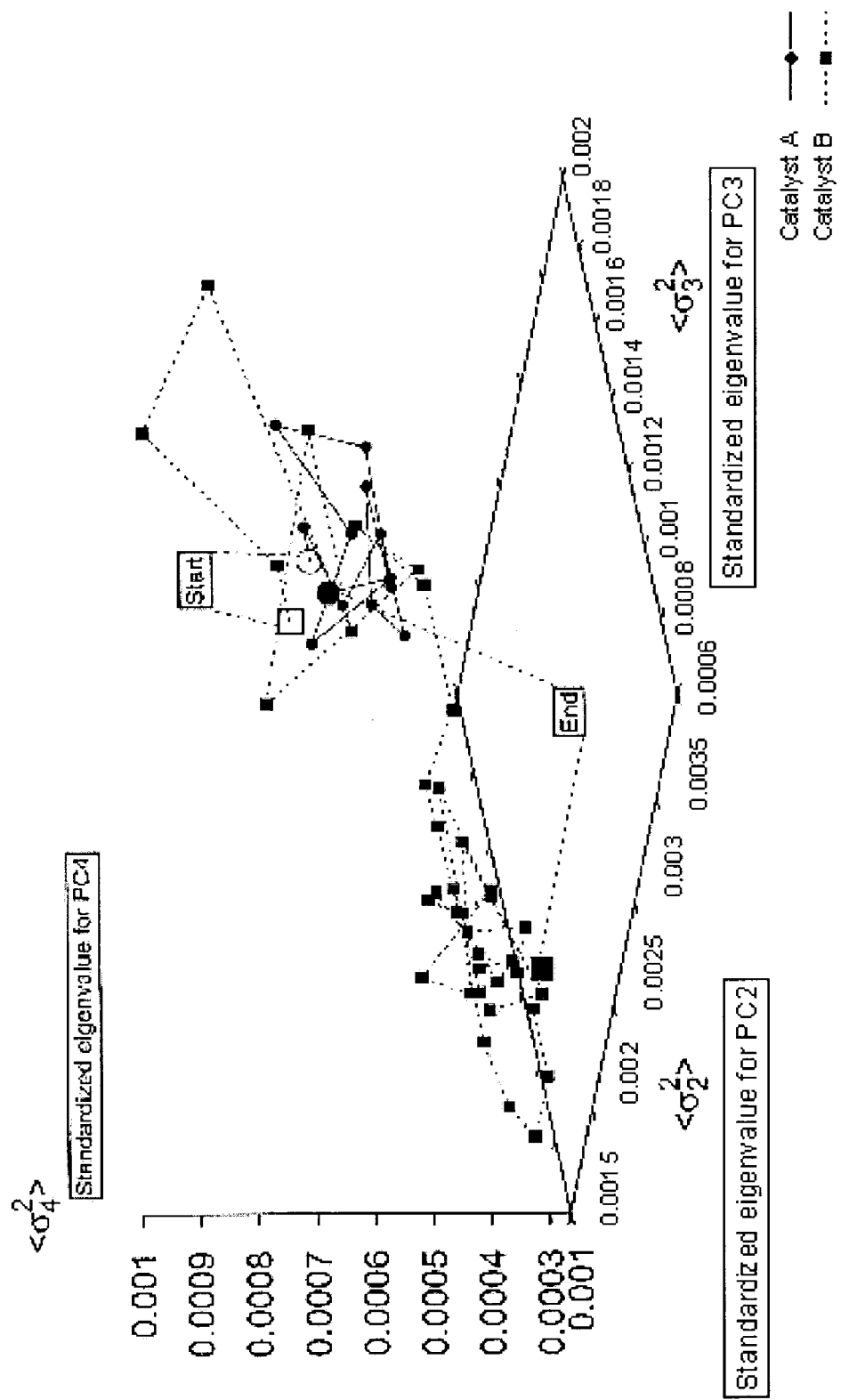
FIG. 13. 3-dimensional illustration using eigenvalues derived from a plurality of filtered signals.
Figure 14:
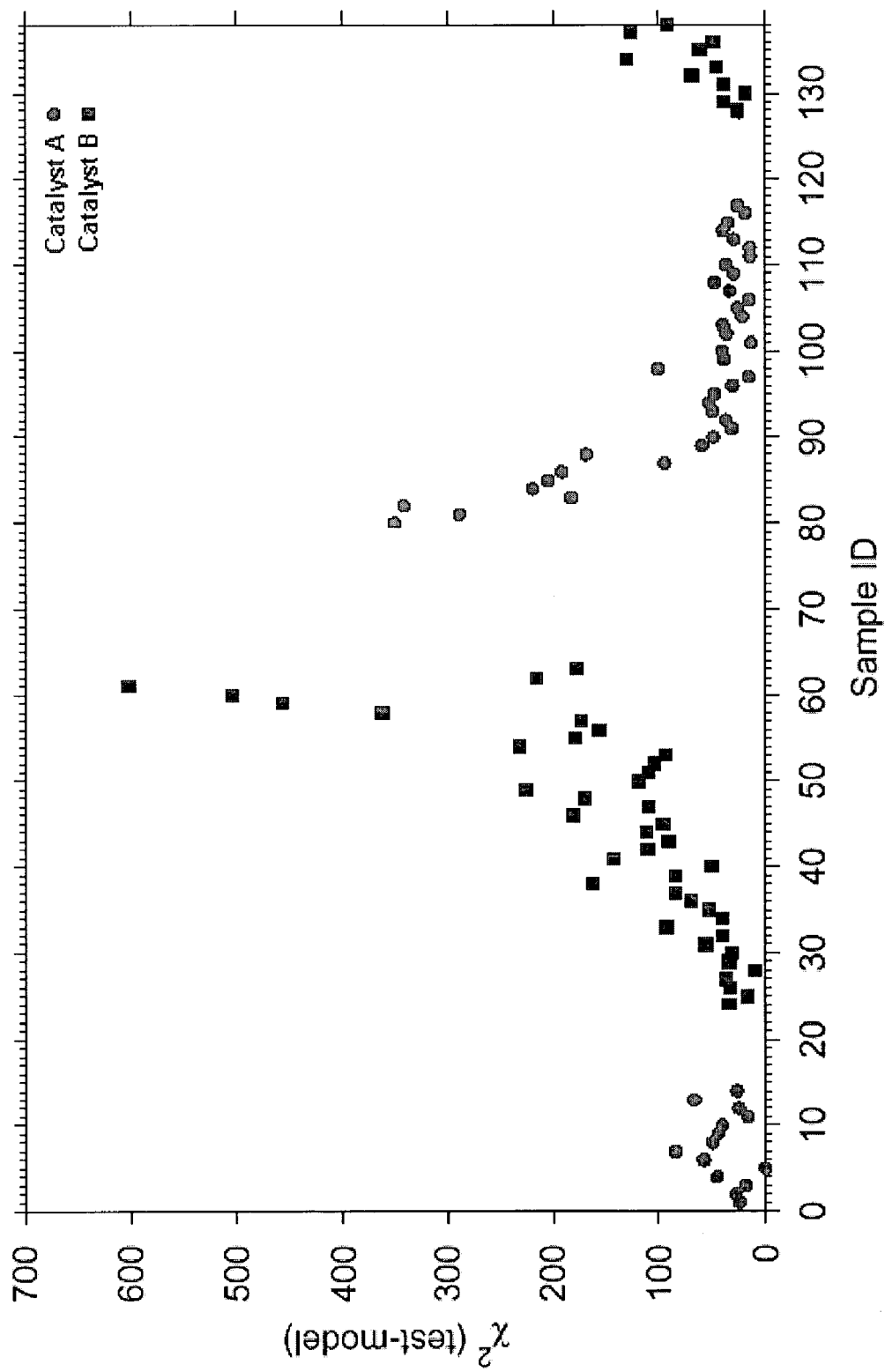
FIG. 14. Graph of different catalysts producing filtered signals analyzed by principal components.

An eigenvalue equation is used to quantify observable entities and comprise an operator, or a mathematical sequence of operations, as a function (eigenfunction) of the system. The value of the quantity being calculated is the eigenvalue. By standardizing eigenvalues to the eigenvalue of a principal component employing an embedding dimension of 10, a multi-dimensional chart depicting the calculated eigenvalues for a sequence was developed (FIG. 13). The principal component (PC) is calculated for each class effectively splitting the process data into multi-dimensional envelopes. In FIG. 13, the eigenvalues for principal components 2, 3 and 4 were standardized with respect to the first principal component for data obtained on two different catalysts showing the ability to discriminate the transition from one catalyst to another. Large open symbols denote the start of a sequence, and large closed symbols denote the end of a sequence. Principal component 2 standardized by the first principal component was graphed as a function of data points (sample ID) for different catalysts and distinctly indicated changes in reactor continuity (FIG. 14) using a chi-squared ($X^2$) test statistic.

The following documents provide additional teachings towards understanding the present invention: U.S. Pat. Nos. 5,436,304; 5,405,922; 4,803,251; 5,391,657; 6,263,355; 6,122,557; 5,857,978; 5,743,860; and 5,626,145 as well as McKenna, Spitz, *Cokljat AIChEJ*, 45 (1999); Finney C. E. A., Green J. B. Jr., Daw C. S., "Symbolic time-series analysis of engine combustion measurements", *SAE Paper No.* 980624 (1998); Kennel M. B, "Statistical test for dynamical nonstationarity in observed time-series data", *Physical Review E* 56, pp. 316–321 (1997); Packard N., Crutchfield J., Farmer J. D., Shaw R. "Geometry from a time series", *Physical Review Letters* 45, pp. 712–716 (1980); Schouten J. C., Takens F., van den Bleek C. M., "Maximum-likelihood estimation of the entropy of an attractor", *Physical Review E* 49, pp. 126–129 (1994); Schouten J. C., van den Bleek C. M., "Monitoring the quality of fluidization using the short-term predictability of pressure fluctuations", *AIChE Journal* 44: 48–60 (1998); and Tang X. Z., Tracy E. R., "Data compression and information retrieval via symbolization", *Chaos* 8, pp. 688–696 (1998), the disclosures of all of which are incorporated herein by reference.

We claim:

1. A method of determining a reactor continuity comprising the steps of:
    a. measuring system variables of the reactor during a time period to generate data, said variables comprising an acoustic emission, a differential pressure, a bed total pressure drop, a fluidized bulk density, a static voltage and a skin thermocouple measurement;
    b. filtering said data;
    c. calculating a signal from said filtered data employing chaotic non-linear dynamics wherein said signal comprises entropy, cycle time or mean deviation (MD); and
    d. comparing said calculated signal for said reactor to a calculated signal of a control reactor to detect reactor continuity comprising, detecting fluidization changes in the reactor, detecting sheeting or identifying sheeting precursors;
    wherein said reactor is an ethylene gas-phase polymerization reactor.

2. The method of claim 1, wherein said acoustic emission is measured with a passive acoustic emission detector.

3. The method of claim 1, wherein said data comprises high speed data obtained at a collection rate greater than 1 Hz, recorded at least at 10 data points per second for a duration of 1–60 minutes.

4. The method of claim 3, wherein said high speed data set is selected from the group consisting of a fluidized bulk density, a bed total pressure drop, a static voltage, an acoustic emission and a skin thermocouple measurement.

5. The method of claim 1, wherein said signal comprises entropy.

6. The method of claim 1, wherein said signal comprises said cycle time.

7. The method of claim 1, wherein said signal comprises said mean deviation.

8. The method of claim 1, wherein said filtering comprises a root mean square filter.

9. The method of claim 1, wherein said filtering comprises a low pass filter.

10. The method of claim 1, wherein said acoustic emission is measured at about 100 kHz to 400 kHz.

11. The method of claim 1, wherein the determination is performed locally.

12. The method of claim 1, wherein the determination is performed remotely.

13. The method of claim 1 further comprising:
applying a counter measure to control reactor continuity when a difference between the signal for the control reactor and the signal for the reactor being controlled is one of mean deviation decrease, entropy decrease, or cycle time increase.

14. The method of claim 13, wherein said signal comprises eigenvalues of an embedded time series.

15. The method of claim 13, wherein said counter measure comprises injecting poisons into said reactor.

16. The method of claim 13, wherein said counter measure comprises adding anti-static and pro-static agents into said reactor.

17. The method of claim 13, wherein said counter measure comprises adjusting a temperature of said reactor.

18. The method of claim 13, wherein said counter measure comprises adjusting a velocity of a medium in said reactor.

19. The method of claim 13, wherein said counter measure comprises adding a reactor surface modifier to said reactor.

20. The method of claim 13, wherein said counter measure comprises adding a gas pulse to said reactor.

21. The method of claim 13, wherein the counter measure control is performed locally.

22. The method of claim 13, wherein the counter measure control is performed remotely.

23. The method of claim 13, wherein the determination is performed locally and the counter measure control is performed locally.

24. The method of claim 13, wherein the determination is performed locally and the counter measure control is performed remotely.

25. The method of claim 13, wherein the determination is performed remotely and the counter measure control is performed locally.

26. The method of claim 13, wherein the determination is performed remotely and the counter measure control is performed remotely.

27. A method of determining a reactor continuity comprising the steps of:
a. measuring system variables of the reactor during a time period to generate data, said variables consisting essentially of an acoustic emission, a differential pressure, a bed total pressure drop, a fluidized bulk density, a static voltage and a skin thermocouple measurement;
b. filtering said data;
c. calculating a signal from said filtered data employing chaotic non-linear dynamics wherein said signal comprises entropy, cycle time or mean deviation (MD); and
d. comparing said calculated signal for said reactor to a calculated signal of a control reactor to detect reactor continuity comprising, detecting fluidization changes in the reactor, detecting sheeting or identifying sheeting precursors;
wherein said reactor is an ethylene gas-phase polymerization reactor.

* * * * *

UNITED STATES PATENT AND TRADEMARK OFFICE
CERTIFICATE OF CORRECTION

PATENT NO.       : 7,226,789 B2                                    Page 1 of 1
APPLICATION NO.  : 10/298311
DATED            : June 5, 2007
INVENTOR(S)      : Muhle et al.

It is certified that error appears in the above-identified patent and that said Letters Patent is hereby corrected as shown below:

Title page, item (73) Assignee: change "Unication Technolofies, LLC" to --Univation Technologies, LLC--.

Signed and Sealed this

Tenth Day of July, 2007

JON W. DUDAS
*Director of the United States Patent and Trademark Office*